United States Patent
Miyawaki et al.

(10) Patent No.: US 8,603,497 B2
(45) Date of Patent: Dec. 10, 2013

(54) COMPOSITION FOR LOCAL ANESTHESIA

(75) Inventors: Takuya Miyawaki, Okayama (JP); Tatsushi Yoshitomi, Okayama (JP)

(73) Assignee: National University Corporation Okayama University, Okayama (JP)

( * ) Notice: Subject to any disclaimer, the term of this patent is extended or adjusted under 35 U.S.C. 154(b) by 252 days.

(21) Appl. No.: 13/123,545

(22) PCT Filed: Oct. 29, 2009

(86) PCT No.: PCT/JP2009/005718
§ 371 (c)(1),
(2), (4) Date: May 31, 2011

(87) PCT Pub. No.: WO2010/050211
PCT Pub. Date: May 6, 2010

(65) Prior Publication Data
US 2011/0230534 A1    Sep. 22, 2011

(30) Foreign Application Priority Data
Oct. 30, 2008   (JP) ................................ 2008-279142

(51) Int. Cl.
A61K 9/00     (2006.01)
A61K 31/135   (2006.01)
A61K 31/425   (2006.01)

(52) U.S. Cl.
USPC ............................ 424/400; 514/653; 514/365

(58) Field of Classification Search
USPC .................................. 424/400; 514/653, 365
See application file for complete search history.

(56) References Cited

U.S. PATENT DOCUMENTS

| | | | |
|---|---|---|---|
| 5,942,241 A * | 8/1999 | Chasin et al. | 424/426 |
| 6,008,256 A | 12/1999 | Haraguchi et al. | |
| 2002/0044966 A1 * | 4/2002 | Bartholomaeus et al. | 424/468 |
| 2004/0072792 A1 | 4/2004 | Haraguchi et al. | |
| 2006/0211665 A1 * | 9/2006 | Ranawat et al. | 514/171 |
| 2006/0216245 A1 | 9/2006 | Haraguchi et al. | |

FOREIGN PATENT DOCUMENTS

| | | |
|---|---|---|
| JP | 11-315029 | 11/1999 |
| JP | 2002-069006 | 3/2002 |
| JP | 2005-255663 | 9/2005 |
| WO | 2004010894 A2 | 2/2004 |

OTHER PUBLICATIONS

Seuwen et al., Alpha 2-adrenergic agonists stimulate DNA synthesis in Chinese hamster lung fibroblasts transfected with a human alpha 2-adrenergic receptor gene, Cell Regul. May 1990;1(6), printed from http://www.ncbi.nlm.nih.gov/pubmed/1981685, Abstract only, 1 page.*

(Continued)

*Primary Examiner* — Gigi Huang
(74) *Attorney, Agent, or Firm* — Kilyk & Bowersox, P.L.L.C.

(57) ABSTRACT

An object of the present invention is to provide a composition for local anesthesia to be added to a local anesthetic drug, the composition showing a sustained local anesthetic effect and having high safety. The object is achieved by a composition for local anesthesia including a drug antagonistic to a systemic action of adrenaline, i.e., an α2 receptor agonist. The α2 receptor agonist can be added to a local anesthetic agent together with adrenaline or a salt thereof to reduce the amount of adrenaline to be added as compared to that of adrenaline or a salt thereof alone. As a result, a sustained local anesthetic effect is obtained and local anesthesia can be performed with high safety.

3 Claims, 2 Drawing Sheets

(56) References Cited

OTHER PUBLICATIONS

Starke, "alpha-Adrenoceptor Subclassification," Rev. Physiol. Biochem. Pharmacol., vol. 88, 1981, pp. 199-236.
Wright et al., "The relationship between density of alpha-adrenoceptor binding sites and contractile responses in several porcine isolated blood vessels," British Journal of Pharmacology, No. 114, 1995, pp. 678-688.
Goto, "Studies on mechanism of action of vasoconstrictors as potentiator in local anesthesia," Tohoku University Shigaku Zasshi, No. 7, 1988, pp. 1-23 (in Japanese with partial English translation).
Takaishi et al., "A Comparison of Dexmedetomidine versus Propofol for Conscious Sedation during Oral Surgery," Journal of Japanese Dental Society of Anesthesiology, vol. 35, No. 2, 2007, pp. 218-223 (English Abstract only—1 page).
Takahashi et al., Yotsui Tsuikyu Setsujo Jutsu o Sekizui Kumomakuka Masui to Dexmedetomidine Chinsei de Kanri shita Ichi Shorei, Masui, vol. 56, No. 8, 2007, p. 980 (partial English translation attached—3 pages).
Jense et al., "Dexmedetomidine Sedation for Laryngeal Framework Surgery," Annals of Otology, Rhinology, and Laryngology, vol. 117, No. 9, Sep. 2008, pp. 659-664.
Goksu et al., "Effects of dexmedetomidine infusion in patients undergoing functional endoscopic sinus surgery under local anaesthesia," European Journal of Anaesthesiology, vol. 25, No. 1, Jan. 2008, pp. 22-28.
Yoshitomi et al., "Dexmedetomidine Enhances the Local Anesthetic Action of Lidocaine via an alpha-2A Adrenoceptor," Anesth. Analg., vol. 107, No. 1, Jul. 2008, pp. 96-101.
Memis et al, "Adding Dexmedetomidine to Lidocaine for Intravenous Regional Anesthesia," Anesth. Analg., vol. 98, No. 3, 2004, pp. 835-840.
New Yakurigaku (revised 4th Edition), Nankodo Co., Ltd., 2002, pp. 271-275 (in Japanese with partial English translation attached).
Oriol-Lopez et al., "Peridural dexmedetomidine in local anesthesia in order to decrease anxiety," Revista Mexicana de Anesthesiologia, vol. 31, No. 4, 2008, pp. 271-277 (in Spanish with English Abstract attached).
International Search Report for corresponding International Patent Application No. PCT/JP2009/005718 dated Dec. 28, 2009 (2 pages).

\* cited by examiner

Figure 1

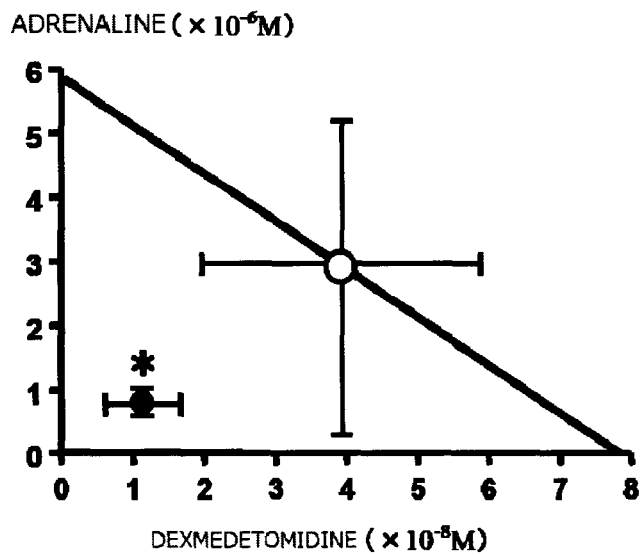

Isobolographic analysis

O: THEORETICAL ED50 VALUE
ADRENALINE: $2.96 \times 10^{-6}$ M ($0.30 \times 10^{-6} - 5.21 \times 10^{-6}$ M)
DEXMEDETOMIDINE: $3.92 \times 10^{-8}$ M ($1.98 \times 10^{-8} - 5.21 \times 10^{-8}$ M)

●: ED50 VALUE OBTAINED IN EXPERIMENT
ADRENALINE: $7.88 \times 10^{-7}$ M ($5.99 \times 10^{-7} - 1.04 \times 10^{-6}$ M)*
DEXMEDETOMIDINE: $1.13 \times 10^{-8}$ M ($7.64 \times 10^{-9} - 1.66 \times 10^{-8}$ M)*

*SIGNIFICANTLY DIFFERENT FROM THEORETICAL ED50 VALUE
$p < 0.05$ (T-test)

EACH RANGE INDICATES MEAN±95% CONFIDENCE INTERVAL.

COMPOSITION FOR LOCAL ANESTHESIA

The present application is a National Stage Application of PCT/JP2009/005718, filed Oct. 29, 2009, which claims priority from Japanese Patent Application No. 2008-279142, which are hereby incorporated by reference.

TECHNICAL FIELD

The present invention relates to a composition for local anesthesia to be added to a local anesthetic agent, and more specifically, to a composition for local anesthesia including an α2 adrenoreceptor (hereinafter, simply referred to as "α2 receptor") agonist.

BACKGROUND ART

It is said that the history of anesthesia started from ether general anesthesia by a dentist E. G. T. Morton publicly in 1846. In 1884, 38 years later, local anesthesia started to be applied in a clinical setting in ophthalmology. As described above, the history of local anesthesia is shorter than that of general anesthesia. In 1885, being the next year, the local anesthesia also started to be applied to dental therapies. In accordance with its applications to a wider variety of surgeries, the local anesthesia has mainly been demanded for providing a long-term sustained action and strong local anesthesia, but is still a developing technology. An effect of the same local anesthetic agent is proportional to an amount of the local anesthetic agent to be used, and hence the use in a large amount also enhances the effect. However, because intoxication due to the use in a large amount causes a threat to life, the amount of the local anesthetic agent to be used is limited as a matter of course.

In view of the foregoing, in clinical practice, a local anesthetic agent having added thereto a composition for local anesthesia (mainly vasoconstriction) may be used in order to prolong the duration of a local anesthetic action and to enhance anesthesia. For example, dental therapies require strong local anesthesia to anesthetize the nerve at the tip of the root of a tooth embedded in the bone, and further require a long-term local anesthetic action to remove a wisdom tooth embedded in the bone. Thus, the local anesthetic agent having added thereto a composition for local anesthesia is generally used.

The composition for local anesthesia is added for the purposes such as: (1) enhancing a local anesthetic effect; (2) locally retaining a local anesthetic agent to prolong an anesthetic duration; (3) delaying the absorption of local anesthesia to prevent the appearance of intoxication; (4) reducing the amount of a local anesthetic agent to be used; and (5) suppressing bleeding from a surgical field to provide a sufficient visual field (see Dental anesthesiology, 6th edition, Chapter 4 Local anesthetic method). As described above, the composition for local anesthesia has various advantages in addition to the prolonged duration of action and the anesthesia enhancing action. At present, adrenalines (including adrenaline, epinephrine tartrate, and other catecholamines) and polypeptides such as felypressin are used as the composition for local anesthesia. Among ones which may be generally used, adrenaline or a salt thereof is most effective and is used frequently at a concentration of 2.73 to $7.6 \times 10^{-5}$ M.

Adrenaline or a salt thereof serving as a vasoconstrictor at a concentration of 2.73 to $7.6 \times 10^{-5}$ M is effective and hence is used as the composition for local anesthesia most frequently from the past up to the present. However, it has been reported that, in the case of administering a local anesthetic agent having added thereto a composition for local anesthesia including adrenaline or a salt thereof, adrenaline in the composition for local anesthesia acts on not only an injection site but also a systemic body, resulting in specific severe adverse effects such as an increase in blood pressure or an adverse influence on the heart. It is therefore necessary to carefully administer the local anesthetic agent to older people (local anesthetic agent: lidocaine hydrochloride-adrenaline injection, see package insert). Further, a local anesthetic agent having added thereto a vasoconstrictor including adrenaline or a salt thereof may exacerbate medical conditions of patients suffering from, for example, hypertension, arteriosclerosis, heart failure, hyperthyroid, and diabetes, and is hence contraindicated for use in those patients in principle (local anesthetic agent: lidocaine hydrochloride-adrenaline injection, see package insert). Further, from the viewpoint of drug interactions, when patients constantly take a β receptor blocker, a tricyclic antidepressant, a butyrophenone drug, an α receptor blocker, a digitalis preparation, quinidine, a β receptor agonist, an antidiabetic, or the like, the combined use should be undertaken with care (local anesthetic agent: lidocaine hydrochloride-adrenaline injection, see package insert).

A composition for local anesthesia as an alternative to adrenaline or a salt thereof is under development. Felypressin as a polypeptide is a composition for local anesthesia which is generally used except adrenaline but shows a lower efficacy than adrenaline or a salt thereof and is hence not frequently used. In addition, although it is said that acidic mucopolysaccharides, a cellulose derivative, maltosyl β-cyclodextrin, salicylic acid, an antihistamine agent, and the like each have such action, those have not yet been put to practical and general use (Patent Literatures 1 to 5). It is conceivable that any such substance alone lacks superiority enough to serve as an alternative to adrenaline or a salt thereof. Meanwhile, researches on compositions from the viewpoint of suppressing adverse effects by reducing the amount of adrenaline or a salt thereof have also been carried out, but also in this case, the compositions are not practical in terms of, for example, drug particularity and complexity (Patent Literatures 6 and 7).

There is a report that a local anesthetic action is enhanced by adding dexmedetomidine serving as an α2 receptor agonist as a novel composition for local anesthesia to a local anesthetic agent (Non Patent Literature 1). Further, there is given an aid for an anesthetic agent for pain control and neurologic inflammation as one of the fields which may be treated with an α-2 receptor agonist (α2 receptor agonist) (Patent Literature 8). A number of reports have demonstrated that the α2 receptor agonist as a preanesthetic medication has sedative and antianxiety actions and reduces the amount of an analgesic drug required in the perioperative period. For the local anesthetic agent, however, a composition for local anesthesia including adrenaline and an α2 receptor agonist has not been reported heretofore. Adrenaline is an agonist acting on both of an α1 receptor and an α2 receptor, whereas dexmedetomidine is an agonist highly selective for the α2 receptor. As for actions of an α1 receptor agonist and an α2 receptor agonist, the idea that the α1 receptor agonist gives an additive effect and the α2 receptor agonist reduces the effect in a sympathetic response (Starke K: α-Adrenoceptor subclassification.: Non Patent Literature 2) is general. Further, research on binding to receptors (Wright I K, et al.: Non Patent Literature 3) has demonstrated that the binding to the α1 receptor and the α2 receptor in large blood vessels is also additive or weakly counteracting. There is also a report that the preadministration of yohimbine serving as an α2 receptor antagonist had no influence on a local anesthesia enhancing action of adrenaline (Kippei Goto: Research on action mechanism of vasoconstrictor as local anesthetic action enhancing substance: Non Patent Literature 4).

CITATION LIST

Patent Literature

[PTL 1] JP 2002-275093 A
[PTL 2] JP 2005-255663 A
[PTL 3] JP 2002-69006 A
[PTL 4] JP 11-315029 A
[PTL 5] WO 2004/052399 A1
[PTL 6] JP 406884 B2
[PTL 7] WO 97/07794 A1
[PTL 8] WO 2004/010894 A1 (JP 2006-504661 A)

Non Patent Literature

[NPL 1] Anesth Analg 107: 96-101 (2008)
[NPL 2] Physiol Biochem Pharmacol 88: 199-236 (1981)
[NPL 3] Br J Pharmacol 114: 678-688 (1995)
[NPL 4] Tohoku University Dental Journal 7: 1-12 (1988)

DISCLOSURE OF INVENTION

Technical Problem

An object of the present invention is to provide a composition for local anesthesia to be added to a local anesthetic agent, the composition showing a sustained local anesthetic effect and having high safety.

Solution to Problem

The inventors of the present invention have made extensive studies in order to solve the above-mentioned problem. As a result, the inventors have found that the above-mentioned problem is solved by incorporating a drug antagonistic to a systemic action of adrenaline, i.e., an α2 receptor agonist into a composition for local anesthesia. Thus, the present invention has been completed.

That is, the present invention includes the following.

1. A composition for local anesthesia to be added to a local anesthetic agent, the composition including an α2 receptor agonist.
2. A composition for local anesthesia according to the item 1, in which the α2 receptor agonist is dexmedetomidine or a salt thereof.
3. A composition for local anesthesia according to the item 1 or 2, in which the α2 receptor agonist is included at a concentration of $1 \times 10^{-15}$ M or more and $1 \times 10^{-6}$ M or less.
4. A composition for local anesthesia according to any one of the items 1 to 3, further including adrenaline or a salt thereof.
5. A composition for local anesthesia according to the item 4, in which the adrenaline or the salt thereof is included at a concentration of $1 \times 10^{-20}$ M or more and $2.7 \times 10^{-5}$ M or less.
6. A composition for local anesthesia according to any one of the items 1 to 5, in which the local anesthetic agent includes lidocaine or a salt thereof as an active ingredient.
7. A local anesthetic agent formulation, including a local anesthetic agent and the composition for local anesthesia according to any one of the items 1 to 6.
8. A kit for local anesthesia, including a local anesthetic agent and the composition for local anesthesia according to any one of the items 1 to 6 as components.

Advantageous Effects of Invention

In the case of using a local anesthetic agent having added thereto adrenaline or a salt thereof, the use of the composition for local anesthesia including an α2 receptor agonist of the present invention can reduce the amount of adrenaline or a salt thereof to be used. As a result, an increase in blood pressure, an adverse influence on the heart, and the like, which are concerned matters in the case of using adrenaline or a salt thereof alone, are reduced. Adrenaline binds to an α receptor and a β receptor in a living body and exerts a range of actions. The α receptor includes two types of receptors, i.e., an α1 receptor and an α2 receptor. The α1 receptor exhibits a vasoconstriction action and has an action of constricting not only local but also systemic blood vessels to increase blood pressure. Meanwhile, the α2 receptor is supposed to have a local vasoconstriction action and a systemic vasodilation action, and to be antagonistic to an action via the α1 receptor through a feedback regulatory function. In view of the foregoing, the α2 receptor agonist included in the composition for local anesthesia of the present invention can suppress a systemic blood pressure increasing action of adrenaline or a salt thereof and can reduce an adverse effect of adrenaline or a salt thereof.

Further, the combined use of the α2 receptor agonist and adrenaline or a salt thereof provides a local anesthetic effect more effectively than the case of adding adrenaline or a salt thereof or the α2 receptor agonist alone to a local anesthetic agent. Hence, the amount of adrenaline or a salt thereof to be used can be reduced, and as a result, an adverse effect due to adrenaline or a salt thereof can also be reduced.

BRIEF DESCRIPTION OF DRAWINGS

FIG. 1 is a graph illustrating results with an isobolographic analysis (Example 1).

DESCRIPTION OF EMBODIMENTS

Figure 2:
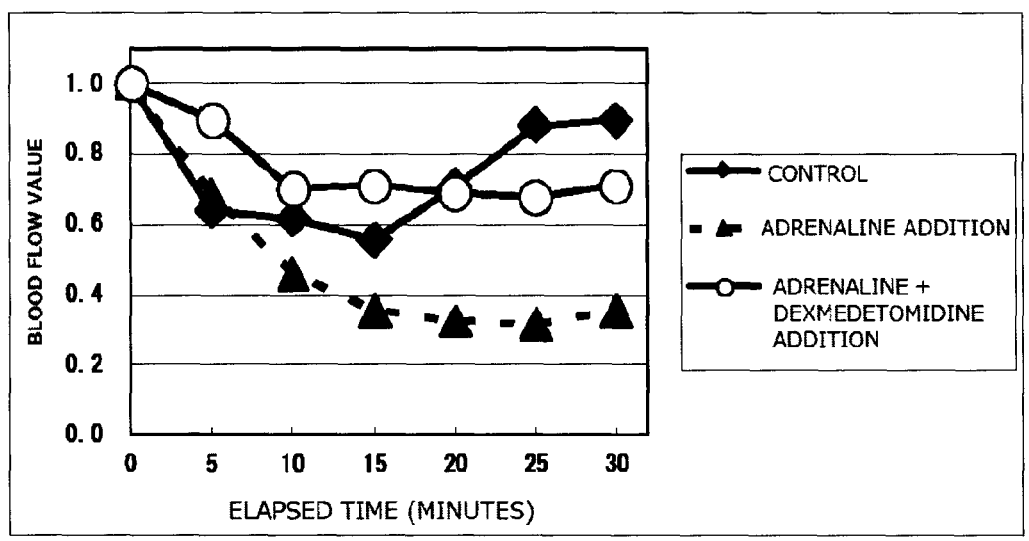
FIG. 2 is a graph illustrating an action of a composition for local anesthesia of the present invention on vasoconstriction (Example 4).

In the present invention, a composition for local anesthesia refers to a composition to be added to a local anesthetic agent and is used for the purposes such as: (1) enhancing a local anesthetic effect; (2) locally retaining a local anesthetic agent to prolong an anesthetic duration; (3) delaying the absorption of local anesthesia to prevent the appearance of intoxication; (4) reducing the amount of a local anesthetic agent to be used; and (5) suppressing bleeding from a surgical field to provide a sufficient visual field.

The composition for local anesthesia of the present invention includes at least an α2 receptor agonist. An α2 receptor is a substance having an antagonistic action against an α1 receptor action in an α receptor. An α1 receptor is involved in general constriction responses such as a vasoconstriction action, whereas the α2 receptor is present in the nerve terminal in the center and suppresses the release of adrenaline to suppress sympathetic excitatory neurotransmission. In the present invention, the α2 receptor agonist is not particularly limited and may be specifically exemplified by dexmedetomidine or a pharmaceutically acceptable salt thereof. In the present invention, the combined use of adrenaline or a salt thereof and an α2 receptor agonist is expected to reduce an adverse effect of adrenaline. Accordingly, in the case of using the local anesthetic agent of the present invention, it is necessary to use adrenaline in addition to the α2 receptor agonist.

Thus, the composition for local anesthesia of the present invention may include not only an α2 receptor agonist but also adrenaline or a salt thereof. Also when the composition for local anesthesia includes only the α2 receptor agonist and is free of adrenaline or a salt thereof, it is suitable to use a local anesthetic agent having added thereto adrenaline or a salt thereof separately.

The α2 receptor agonist to be included in the composition for local anesthesia of the present invention has only to be included at $1\times10^{-15}$ M or more, preferably $1\times10^{-10}$ M or more. Further, the upper limit of the use concentration of the α2 receptor agonist is not particularly limited, and a sufficient effect may be exhibited at a concentration of $1\times10^{-6}$ M or less.

Adrenaline or a salt thereof has only to be included in a trace amount in the composition for local anesthesia of the present invention and the amount is not particularly limited. For example, adrenaline or a salt thereof has only to be included in an amount of $1\times10^{-20}$ M or more. Further, adrenaline or a salt thereof may be used in a conventionally used amount, i.e., at a concentration of less than 2.7 to $7.6\times10^{-5}$ M, and may be used at $1\times10^{-5}$ M or less.

The addition of the α2 receptor agonist can reduce the amount of adrenaline or a salt thereof to be used. The concentrations of adrenaline or a salt thereof and the α2 receptor agonist included in the composition for local anesthesia were a combination of $1\times10^{-5}$ M or less and $1\times10^{-6}$ M or less, respectively, which provides an effect, or were a combination of $1\times10^{-6}$ M and $1\times10^{-7}$ M, respectively, a combination of $1\times10^{-6}$ M and $1\times10^{-8}$ M or less, respectively, or a combination of $1\times10^{-7}$ M and $1\times10^{-7}$ M or less, respectively, which provides a sufficient effect.

In the present invention, the local anesthetic drug as an active ingredient included in the local anesthetic agent has only to be a local anesthetic drug which may be used together with adrenaline or a salt thereof and is not particularly limited. The local anesthetic drug is specifically exemplified by lidocaine or a pharmaceutically acceptable salt thereof.

As described in the section Background Art, a number of reports show that the α2 receptor agonist as a preanesthetic medication has sedative and antianxiety actions and reduces the amount of an analgesic drug required in the perioperative period. For the local anesthetic agent, however, a composition for local anesthesia including adrenaline and an α2 receptor agonist has not been reported heretofore. This is because it was unpredictable that a drug combination of those agonists had a synergistic effect in view of the relationship between the α1 receptor and the α2 receptor. Adrenaline is an agonist acting on both of the α1 receptor and the α2 receptor, whereas dexmedetomidine is an agonist highly selective for the α2 receptor. As for actions of an α1 receptor agonist and an α2 receptor agonist, the idea that the α1 receptor agonist gives an additive effect and the α2 receptor agonist reduces the effect in a sympathetic response (Starke K: α-Adrenoceptor subclassification.: Non Patent Literature 2) is general. Further, research on binding to receptors (Wright I K, et al.: Non Patent Literature 3) has demonstrated that the binding to the α1 receptor and the α2 receptor in large blood vessels is also additive or weakly counteracting.

Based on those findings, when a large factor for enhancing the action of the local anesthetic drug is considered as a vasoconstriction action, a drug combination including adrenaline, which is an agonist for both of the α1 receptor and the α2 receptor, and dexmedetomidine, which is an α2 receptor agonist, is predicted to exhibit an additive or counteracting (antagonistic) action. There is also a report that the preadministration of yohimbine serving as an α2 receptor antagonist had no influence on a local anesthesia enhancing action of adrenaline (Kippei Goto: Research on action mechanism of vasoconstrictor as local anesthetic action enhancing substance: Non Patent Literature 4). It has been demonstrated that the vasoconstriction action via the α1 receptor is larger than the action via the α2 receptor. Accordingly, in view of previous findings and literatures, even when the composition for local anesthesia including adrenaline and dexmedetomidine is added to the local anesthetic agent, probably, the addition can provide neither a synergistic action nor an additive action. However, in the case of the composition for local anesthesia including adrenaline and dexmedetomidine as an embodiment of the present invention, the composition for local anesthesia tends to suppress a vasoconstriction action of adrenaline alone (see Example 4). Thus, it is probable that the effect is not a local anesthesia enhancing effect through a vasoconstriction action but an anesthesia enhancing effect through a novel mechanism. The fact was extremely difficult to be predicted.

In this description, the pharmaceutically acceptable salt is exemplified by general pharmacologically and pharmaceutically acceptable salts. Specific examples of such salts include the following.

There are given base addition salts including: alkali metal salts such as a sodium salt and a potassium salt; alkaline earth metal salts such as a calcium salt and a magnesium salt; for example, an ammonium salt; aliphatic amine salts such as a trimethylamine salt, a triethylamine salt, a dicyclohexylamine salt, an ethanolamine salt, a diethanolamine salt, a triethanolamine salt, and a procaine salt; aralkylamine salts such as an N,N-dibenzylethylenediamine salt; heterocyclic aromatic amine salts such as a pyridine salt, a picoline salt, a quinoline salt, and an isoquinoline salt; quaternary ammonium salts such as a tetramethylammonium salt, a tetraethylammonium salt, a benzyltrimethylammonium salt, a benzyltriethylammonium salt, a benzyltributylammonium salt, a methyltrioctylammonium salt, and a tetrabutylammonium salt; basic amino acid salts such as an arginine salt and a lysine salt; and the like.

There are given acid addition salts including: inorganic acid salts such as a hydrochloride, a sulfate, a nitrate, a phosphate, a carbonate, a hydrogencarbonate, and a perchlorate; organic acid salts such as an acetate, a propionate, a lactate, a maleate, a fumarate, a tartrate, a malate, a citrate, and an ascorbate; sulfonates such as a methanesulfonate, an isethionate, a benzenesulfonate, and a p-toluenesulfonate; acidic amino acid salts such as an aspartate and a glutamate; and the like.

The present invention also encompasses a local anesthetic agent formulation including a local anesthetic agent having added thereto the above-mentioned composition for local anesthesia. A preparation method for the local anesthetic agent formulation is not particularly limited, and the local anesthetic agent formulation may be prepared, for example, by mixing equal amounts of a 2-fold concentrated solution of an effective concentration of a local anesthetic drug and the above-mentioned composition for local anesthesia.

Further, the present invention also encompasses a kit for local anesthesia including a local anesthetic agent and the above-mentioned composition for local anesthesia as components. In the case of the kit, an appropriate amount of the composition for local anesthesia may be mixed into the local anesthetic agent before use or in advance and used. In this case, the blending ratio of the local anesthetic agent and the composition for local anesthesia may be appropriately changed as necessary. The kit may include other solutions and instruments such as a cartridge, a syringe for injection, and an injection needle as appropriate.

EXAMPLES

Hereinafter, the present invention is described more specifically by way of examples. However, the present invention is by no means limited to the range of the following examples.

Example 1

Composition for Local Anesthesia

In this example, mixtures of an α2 receptor agonist (dexmedetomidine) and adrenaline at various concentrations were each used as a composition for local anesthesia, and a local anesthesia enhancing effect in the case of adding the composition for local anesthesia to a local anesthetic agent including lidocaine as an active ingredient was confirmed. In carrying out experiments of this example, in Experiments 1 and 2 described below, a local anesthesia enhancing action in the case of adding dexmedetomidine alone or adrenaline alone to a local anesthetic agent was firstly evaluated. After that, in Experiment 3, based on 50% effective doses (Effective dose 50: ED50) for the respective drugs, mixtures of the respective drugs were each used as a composition for local anesthesia, and a local anesthesia enhancing effect in the case of adding the composition for local anesthesia to a local anesthetic agent was confirmed.

Experiment 1

Local Anesthesia Enhancing Action in Adding Dexmedetomidine Alone to Local Anesthetic Agent Reagents:
Dexmedetomidine hydrochloride (Precedex®: Maruishi Pharmaceutical Co., Ltd.)
236 μg in 2 ml for 1 vial
Lidocaine hydrochloride (Sigma-Aldrich, Inc.)
Physiological saline (Otsuka Pharmaceutical Co., Ltd.)
Blend of Reagents:
123.6 ml of physiological saline were added to 1.0 ml of dexmedetomidine hydrochloride (Precedex®) to prepare Solution (a) at $4 \times 10^{-6}$ M. The solution was diluted 10-fold, 100-fold, and 1000-fold with physiological saline to prepare Solution (b) at $4 \times 10^{-7}$ M, Solution (c) at $4 \times 10^{-8}$ M, and Solution (d) at $4 \times 10^{-9}$ M, respectively. Next, 200 mg of lidocaine hydrochloride were dissolved in 10 ml of physiological saline to prepare Solution (e) at 2%. The above-mentioned solutions were used to blend reagents as shown in Table 1.

TABLE 1

|  | Solution 1 | Solution 2 | Solution 3 | Solution 4 | Solution 5 (Control) |
|---|---|---|---|---|---|
| Dexmedetomidine hydrochloride | Solution (a) 1.0 ml | Solution (b) 1.0 ml | Solution (c) 1.0 ml | Solution (d) 1.0 ml | None |
| Lidocaine hydrochloride | Solution (e) 1.0 ml | Solution (e) 1.0 ml | Solution (e) 1.0 ml | Solution (e) 1.0 ml | Solution (e) 1.0 ml |
| Physiological saline | 2.0 ml | 2.0 ml | 2.0 ml | 2.0 ml | 3.0 ml |

Experimental Method:
A guinea pig wheal method was employed. The hair on the back of Hartley male guinea pigs each having a body weight of 500 to 600 g was clipped. After that, 0.1 ml each of Solutions 1 to 5 blended as described above was injected intracutaneously, and the surroundings of wheals, which developed in the skin, were marked with a felt-tipped pen. Pricks were applied on six sites inside each wheal with a fixed-weight sensory needle. The number of times that the prick failed to elicit a constriction response, i.e., the number of times that the solution was judged to have an anesthetic effect was measured. The pricks were applied every 5 minutes until 60 minutes, and the total of the number of times that an anesthetic effect was observed was used as a score to assess the durability of a local anesthetic action. A 50% effective dose (effective dose 50: ED50) for dexmedetomidine was calculated based on a score for each of Solutions 1 to 5. As a result, as shown in Table 2, the ED50 value for dexmedetomidine hydrochloride was found to be $7.83 \times 10^{-8}$ M.

TABLE 2

|  | Solution 1 | Solution 2 | Solution 3 | Solution 4 | Solution 5 |
|---|---|---|---|---|---|
| Dexmedetomidine hydrochloride concentration (M) | $10^{-6}$ | $10^{-7}$ | $10^{-8}$ | $10^{-9}$ | 0 |
| Score | 44.3 ± 4.0* | 33.2 ± 4.7* | 26.0 ± 3.0 | 20.6 ± 3.3 | 20.1 ± 2.9 |
| ED50 |  |  | $7.83 \times 10^{-8}$ M |  |  |

*Significantly different from control value P < 0.05 (Dunnet method)

Experiment 2

Local Anesthesia Enhancing Action in Adding Adrenaline Alone to Local Anesthetic Agent Reagents:
Japanese Pharmacopoeia adrenaline injection (Bosmin Injection®: DAIICHI SANKYO COMPANY, LIMITED) 1 mg in 1 ml
Lidocaine hydrochloride (Sigma-Aldrich, Inc.)
Physiological saline (Otsuka Pharmaceutical Co., Ltd.)

Blend of Reagents:
12.7 ml of physiological saline were added to 1.0 ml of a Japanese Pharmacopoeia adrenaline injection (Bosmin Injection®) to prepare Solution (f) at $4.0 \times 10^{-4}$ M. Solution (f) was diluted 10-fold, 100-fold, and 1000-fold to prepare Solution (g) at $4 \times 10^{-5}$ M, Solution (h) at $4 \times 10^{-6}$ M, and Solution (i) at $4 \times 10^{-7}$ M, respectively. Reagents were blended as described below to evaluate an effect of adrenaline. Solution (e), which was the same as that in Experiment 1 described above, was used as lidocaine hydrochloride. The above-mentioned solutions were used to blend reagents as described below.

TABLE 3

|  | Solution 6 | Solution 7 | Solution 8 | Solution 9 | Solution 10 (Control) |
|---|---|---|---|---|---|
| Japanese Pharmacopoeia adrenaline injection | Solution (f) 1.0 ml | Solution (g) 1.0 ml | Solution (h) 1.0 ml | Solution (i) 1.0 ml | None |
| Lidocaine hydrochloride | Solution (e) 1.0 ml | Solution (e) 1.0 ml | Solution (e) 1.0 ml | Solution (e) 1.0 ml | Solution (e) 1.0 ml |
| Physiological saline | 2.0 ml | 2.0 ml | 2.0 ml | 2.0 ml | 3.0 ml |

Experimental Method:
A guinea pig wheal method was employed in the same manner as in Experiment 1 described above. An ED50 value for adrenaline was calculated based on a score for each of Solutions 6 to 10. As a result, as shown in Table 4, the ED50 value for adrenaline was found to be $5.91 \times 10^{-6}$ M.

TABLE 4

|  | Solution 6 | Solution 7 | Solution 8 | Solution 9 | Solution 10 |
|---|---|---|---|---|---|
| Adrenaline concentration (M) | $10^{-4}$ | $10^{-5}$ | $10^{-6}$ | $10^{-7}$ | 0 |
| Score | 58.3 ± 6.5* | 42.1 ± 5.9* | 24.1 ± 3.6 | 25.6 ± 6.0 | 18.4 ± 4.5 |
| ED50 |  |  | $5.91 \times 10^{-6}$ M |  |  |

*Significantly different from control value $P < 0.05$ (Dunnet method)

Experiment 3

A mixture of dexmedetomidine and adrenaline at each concentration was used as a composition for local anesthesia, and a local anesthesia enhancing action in the case of adding the composition for local anesthesia to a local anesthetic agent was evaluated.

The same dexmedetomidine hydrochloride, Japanese Pharmacopoeia adrenaline injection, lidocaine hydrochloride, and physiological saline as in Experiments 1 and 2 described above were used as reagents. For the respective reagents, based on the respective ED50 values for dexmedetomidine hydrochloride and adrenaline obtained from Experiments 1 and 2 described above, the reagents were blended as described below so that the solutions have final concentrations of 1/2, 1/4, 1/8, and 1/16 of the ED50 values for the respective drugs. Solution (e) was used as a lidocaine hydrochloride solution in the same manner as in Experiments 1 and 2 described above.

TABLE 5

|  | Solution 11 | Solution 12 | Solution 13 | Solution 14 | Solution 15 (Control) |
|---|---|---|---|---|---|
| Japanese Pharmacopoeia | 1.0 ml ½ × ED50 | 1.0 ml ¼ × ED50 | 1.0 ml ⅛ × ED50 | 1.0 ml ¹⁄₁₆ × ED50 | None |

TABLE 5-continued

|  | Solution 11 | Solution 12 | Solution 13 | Solution 14 | Solution 15 (Control) |
|---|---|---|---|---|---|
| adrenaline injection | (final concentration) | (final concentration) | (final concentration) | (final concentration) | |
| Lidocaine hydrochloride | Solution (e) 1.0 ml | Solution (e) 1.0 ml | Solution (e) 1.0 ml | Solution (e) 1.0 ml | Solution (e) 1.0 ml |
| Physiological saline | 1.0 ml | 1.0 ml | 1.0 ml | 1.0 ml | 2.0 ml |
| Dexmedetomidine hydrochloride | 1.0 ml ½ × ED50 (final concentration) | 1.0 ml ¼ × ED50 (final concentration) | 1.0 ml ⅛ × ED50 (final concentration) | 1.0 ml ¹⁄₁₆ × ED50 (final concentration) | None |

Experimental Method:

A guinea pig wheal method was employed in the same manner as in Experiments 1 and 2 described above. Each score for Solutions 11 to 15 was confirmed (Table 6).

TABLE 6

|  | Solution 11 | Solution 12 | Solution 13 | Solution 14 | Solution 15 |
|---|---|---|---|---|---|
| Score | 44.6 ± 6.9* | 37.5 ± 9.1* | 29.5 ± 7.4 | 25.2 ± 4.9 | 18.3 ± 2.8 |

*Significantly different from control value P < 0.05 (Dunnet method)

Based on a score for each of Solutions 11 to 15 and the ED50 values obtained from Experiments 1 and 2, an interaction between dexmedetomidine (Drug 1) and adrenaline (Drug 2) was analyzed with an isobologram (Tallarida R J, et al, Statistical analysis of drug-drug and site-site interactions with isobolograms. Life Sci, 45:947-961, 1989). The ratio of an observed value to a theoretical value for an ED50 value in combined use was defined as a total dose fraction value and was calculated with the following equation (Roerig S C and Fujimoto J M, Morphine antinociception in different strains of mice: relationship of supraspinal-spinal multiplicative interaction to tolerance. J. Pharmacol. Exp. Ther. 247: 603-608, 1988).

Total dose fraction value=[Ratio of observed value to theoretical value of ED50 value in combined use]=[ED50 for dose of Drug 1 in combined use/ED50 for dose of Drug 1 in single use]+[ED50 for dose of Drug 2 in combined use/ED50 for dose of Drug 2 in single use]

The interaction between both drugs was evaluated to be additive, synergistic, and counteracting (antagonistic) when the total dose fraction value was 1, less than 1, and more than 1, respectively (Tallarida R J, et al, Statistical analysis of drug-drug and site-site interactions with isobolograms. Life Sci, 45: 947-961, 1989; Roerig S C and Fujimoto J M, Morphine antinociception in different strains of mice: relationship of supraspinal-spinal multiplicative interaction to tolerance. J. Pharmacol. Exp. Ther. 247: 603-608, 1988; Tallarida R J: Drug synergism and dose-effect data analysis. Chapman & Hall/CRC, Florida, USA, 2000).

FIG. 1 is a graph called an isobologram for the evaluation of an interaction between two drugs. In FIG. 1, the intercept of a graph straight line with the lateral axis indicates ED50 for adrenaline alone and the intercept with the lateral axis indicates ED50 for dexmedetomidine alone. The theoretical ED50 values in the combined use of adrenaline and dexmedetomidine were $2.96 \times 10^{-6}$ M ($0.30 \times 10^{-6}$ to $5.21 \times 10^{-6}$ M) and $3.92 \times 10^{-8}$ M ($1.98 \times 10^{-8}$ to $5.21 \times 10^{-8}$ M), respectively, and were represented on the graph straight line (open circle). In contrast to the theoretical values, the ED50 values obtained in the experiment were $7.88 \times 10^{-7}$ M ($5.99 \times 10^{-7}$ to $1.04 \times 10^{-6}$ M) and $1.13 \times 10^{-8}$ M ($7.64 \times 10^{-9}$ to $1.66 \times 10^{-8}$ M), respectively (filled circle). The results were significantly different from the theoretical ED50 values (P<0.05 (T-test)). Each of the ranges indicates mean±95% confidence interval. The isobolographic analysis reveals the following. When ED50 obtained in the experiment in the combined use of two drugs is positioned on a straight line connecting the ED50 values for the respective drugs alone, the total dose fraction value comes to 1, and hence the concomitant drug can be judged to have an additive action (such an action that actions of both drugs are simply added). When the value is larger than the straight line (region above the straight line), the total dose fraction value comes to more than 1, and hence the concomitant drug can be judged to have a counteracting action (antagonistic action: such an action that actions of both drugs are reduced). When the value is smaller than the straight line (region below the straight line), the total dose fraction value comes to less than 1, and hence the concomitant drug can be judged to have a synergistic action (larger action than the addition of actions of both drugs) (Tallarida R J, et al, Statistical analysis of drug-drug and site-site interactions with isobolograms. Life Sci, 45: 947-961, 1989; Roerig S C and Fujimoto J M, Morphine antinociception in different strains of mice: relationship of supraspinal-spinal multiplicative interaction to tolerance. J. Pharmacol. Exp. Ther. 247: 603-608, 1988; Tallarida R J: Drug synergism and dose-effect data analysis. Chapman & Hall/CRC, Florida, USA, 2000).

In the experimental results, the theoretical ED50 values in adrenaline and dexmedetomidine were $2.96 \times 10^{-6}$ M ($0.30 \times 10^{-6}$ to $5.21 \times 10^{-6}$M) and $3.92 \times 10^{-8}$ M ($1.98 \times 10^{-8}$ to $5.21 \times 10^{-8}$M), respectively, whereas the ED50 values obtained in the experiment were $7.88 \times 10^{-7}$ M ($5.99 \times 10^{-7}$ to $1.04 \times 10^{-6}$ M) and $1.13 \times 10^{-8}$ M ($7.64 \times 10^{-9}$ to $1.66 \times 10^{-8}$ M), respectively. Those results were significantly different from the theoretical ED50 values (P<0.05 (T-test)). It should be noted that each of the concentration ranges described above indicates mean±95% confidence interval. Further, the total dose fraction value in adrenaline and dexmedetomidine was 0.55.

The above-mentioned results showed that the total dose fraction value was less than 1, and as illustrated in FIG. 1, was positioned in a statistically significant lower region than a straight line connecting the ED50 values (intercept in longitudinal axis: ED50 for adrenaline; intercept in lateral axis: ED50 for dexmedetomidine) obtained in adrenaline alone and dexmedetomidine alone, revealing that the combined use, i.e., drug combination of adrenaline and dexmedetomidine had a synergistic action.

As described above, as a result of the isobolographic analysis, a local anesthesia enhancing action was synergistically observed in the case of adding the composition for local anesthesia including a mixture of adrenaline and dexmedetomidine to the local anesthetic agent including lidocaine hydrochloride as an active ingredient. Accordingly, a composition for local anesthesia (drug combination of adrenaline and dexmedetomidine) obtained by adjusting the blending ratio of adrenaline and dexmedetomidine was found to allow the amount of adrenaline to be added to a local anesthetic agent to be reduced than ever before and to have a local anesthesia enhancing action equal to or higher than ever before.

Example 2

Composition for Local Anesthesia 2

In this example, a local anesthesia enhancing effect in the case of adding adrenaline alone as a composition for local anesthesia to a local anesthetic agent was compared with a local anesthesia enhancing effect in the case of adding a composition for local anesthesia including a mixture of adrenaline and an α2 receptor agonist (dexmedetomidine) to a local anesthetic agent. In this example, in the same manner as in Example 1, a Japanese Pharmacopoeia adrenaline injection (Bosmin Injection®: DAIICHI SANKYO COMPANY, LIMITED), dexmedetomidine hydrochloride (Precedex®: Maruishi Pharmaceutical Co., Ltd.), 236 μg in 2 ml for 1 vial, lidocaine hydrochloride (Sigma-Aldrich, Inc.), and physiological saline (Otsuka Pharmaceutical Co., Ltd.) were used to carry out experiments. Solutions free of adrenaline and dexmedetomidine (Solutions 21 and 27) were each used as a control and Solutions each containing only adrenaline and free of dexmedetomidine (Solutions 16 and 22) were used as comparative examples.

As for reagents, Solution (e), which was the same as that in Experiment 1 of Example 1, was used as lidocaine hydrochloride, and Solution (h) and Solution (i) of Experiment 2 of Example 1 were used as adrenaline. Solution (b), Solution (c), and Solution (d) of Experiment 1 of Example 1, and Solution (j) at $4\times10^{-10}$ M obtained by further diluting Solution (d) 10-fold were used as dexmedetomidine. The solutions were used to prepare reagents as described below.

TABLE 7

|  | Solution 16 | Solution 17 | Solution 18 | Solution 19 | Solution 20 | Solution 21 (Control) |
| --- | --- | --- | --- | --- | --- | --- |
| Japanese Pharmacopoeia adrenaline injection | Solution (h) 1.0 ml | Solution (h) 1.0 ml | Solution (h) 1.0 ml | Solution (h) 1.0 ml | Solution (h) 1.0 ml | None |
| Lidocaine hydrochloride | Solution (e) 1.0 ml | Solution (e) 1.0 ml | Solution (e) 1.0 ml | Solution (e) 1.0 ml | Solution (e) 1.0 ml | Solution (e) 1.0 ml |
| Physiological saline | 2.0 ml | 1.0 ml | 1.0 ml | 1.0 ml | 1.0 ml | 3.0 ml |
| Dexmedetomidine hydrochloride | None | Solution (b) 1.0 ml | Solution (c) 1.0 ml | Solution (d) 1.0 ml | Solution (j) 1.0 ml | None |

TABLE 8

|  | Solution 22 | Solution 23 | Solution 24 | Solution 25 | Solution 26 | Solution 27 (Control) |
| --- | --- | --- | --- | --- | --- | --- |
| Japanese Pharmacopoeia adrenaline injection | Solution (i) 1.0 ml | Solution (i) 1.0 ml | Solution (i) 1.0 ml | Solution (i) 1.0 ml | Solution (i) 1.0 ml | None |
| Lidocaine hydrochloride | Solution (e) 1.0 ml | Solution (e) 1.0 ml | Solution (e) 1.0 ml | Solution (e) 1.0 ml | Solution (e) 1.0 ml | Solution (e) 1.0 ml |
| Physiological saline | 2.0 ml | 1.0 ml | 1.0 ml | 1.0 ml | 1.0 ml | 3.0 ml |
| Dexmedetomidine hydrochloride | None | Solution (b) 1.0 ml | Solution (c) 1.0 ml | Solution (d) 1.0 ml | Solution (j) 1.0 ml | None |

Experimental Method:

A guinea pig wheal method was employed in the same manner as in Experiments 1 to 3 of Example 1 described above. Each score for Solutions 16 to 21 and Solutions 22 to 27 was calculated to assess a local anesthetic effect. As shown in Table 9 and Table 10, the results revealed that the composition for local anesthesia of the present invention including a mixture of adrenaline and a low concentration of dexmedetomidine further enhanced a local anesthetic effect as compared to adrenaline alone (comparative examples).

TABLE 9

|  | Solution 16 | Solution 17 | Solution 18 | Solution 19 | Solution 20 | Solution 21 |
| --- | --- | --- | --- | --- | --- | --- |
| Adrenaline concentration (M) | $10^{-6}$ | $10^{-6}$ | $10^{-6}$ | $10^{-6}$ | $10^{-6}$ | 0 |
| Dexmedetomidine concentration (M) | 0 | $10^{-7}$ | $10^{-8}$ | $10^{-9}$ | $10^{-10}$ | 0 |
| Score | 18 | 32 | 25 | 24 | 23 | 11 |

TABLE 10

|  | Solution 22 | Solution 23 | Solution 24 | Solution 25 | Solution 26 | Solution 27 |
|---|---|---|---|---|---|---|
| Adrenaline concentration (M) | $10^{-7}$ | $10^{-7}$ | $10^{-7}$ | $10^{-7}$ | $10^{-7}$ | 0 |
| Dexmedetomidine concentration (M) | 0 | $10^{-7}$ | $10^{-8}$ | $10^{-9}$ | $10^{-10}$ | 0 |
| Score | 27 | 40 | 34 | 30 | 29 | 23 |

Example 3

Composition for Local Anesthesia 3

In this example, a local anesthesia enhancing effect in the case of adding adrenaline alone as a composition for local anesthesia to a local anesthetic agent at a concentration for general use was compared with a local anesthesia enhancing effect in the case of adding the composition for local anesthesia of the present invention including a mixture of a low concentration of adrenaline and an α2 receptor agonist (dexmedetomidine) as a local anesthetic agent, thereby confirming whether a local anesthesia enhancing effect equal to a conventional local anesthesia enhancing effect was able to be obtained. In this example, in the same manner as in Example 1, a Japanese Pharmacopoeia adrenaline injection (Bosmin Injection®: DAIICHI SANKYO COMPANY, LIMITED), dexmedetomidine hydrochloride (Precedex®: Maruishi Pharmaceutical Co., Ltd.), 236 μg in 2 ml for 1 vial, lidocaine hydrochloride (Sigma-Aldrich, Inc.), and physiological saline (Otsuka Pharmaceutical Co., Ltd.) were used to carry out experiments. A solution free of adrenaline and dexmedetomidine (Solution 31) was used as a control and a solution containing only adrenaline and free of dexmedetomidine (Solution 28) was used as a comparative example.

As for reagents, Solution (e), which was the same as that in Experiment 1 of Example 1, was used as lidocaine hydrochloride, and Solution (h) and Solution (i) of Experiment 2 of Example 1 were used as adrenaline. Solution (b) and Solution (c) of Experiment 2 of Example 1 were used as dexmedetomidine. Further, Solution (k) at an adrenaline concentration of $4 \times 7.6 \times 10^{-5}$ M for clinical use was prepared for a comparative example. The solutions were used to prepare reagents as shown in Table 11.

TABLE 11

|  | Solution 28 | Solution 29 | Solution 30 | Solution 31 (Control) |
|---|---|---|---|---|
| Japanese Pharmacopoeia adrenaline injection | Solution (k) 1.0 ml | Solution (h) 1.0 ml | Solution (i) 1.0 ml | None |
| Lidocaine hydrochloride | Solution (e) 1.0 ml | Solution (e) 1.0 ml | Solution (e) 1.0 ml | Solution (e) 1.0 ml |
| Physiological saline | 2.0 ml | 1.0 ml | 1.0 ml | 3.0 ml |
| Dexmedetomidine hydrochloride | None | Solution (c) 1.0 ml | Solution (b) 1.0 ml | None |

Experimental Method:

A guinea pig wheal method was employed in the same manner as in Experiments 1 to 3 of Example 1 described above. Each score for Solutions 28 to 31 was calculated to assess a local anesthetic effect. As shown in Table 12, the results revealed that, even at an adrenaline concentration about 70- to 700-fold lower than an adrenaline concentration ($7.6 \times 10^{-5}$ M) for clinical use, the same level of a local anesthesia enhancing effect was attained by the mixing of a low concentration of dexmedetomidine.

TABLE 12

|  | Solution 28 | Solution 29 | Solution 30 | Solution 31 |
|---|---|---|---|---|
| Adrenaline concentration (M) | $7.6 \times 10^{-5}$ | $10^{-6}$ | $10^{-7}$ | 0 |
| Dexmedetomidine concentration (M) | 0 | $10^{-8}$ | $10^{-7}$ | 0 |
| Score | 38 | 35 | 35 | 18 |

Example 4

Effect of Composition for Local Anesthesia on Vasoconstriction

A local anesthesia enhancing effect of adrenaline in the case of adding adrenaline to a local anesthetic agent is assumed to result from the absorption inhibition of the local anesthetic agent through peripheral vasoconstriction. Thus, in order to evaluate whether the synergistic effect is exhibited by further enhancement of a peripheral blood vessel enhancing action of adrenaline by dexmedetomidine, or the synergistic effect is exhibited through another mechanism, an influence of dexmedetomidine on a peripheral vasoconstriction action of adrenaline was investigated.

The same dexmedetomidine hydrochloride, Japanese Pharmacopoeia adrenaline injection, lidocaine hydrochloride, and physiological saline as in Experiments 1 and 2 of Example 1 described above were used as reagents. Solution (e), which was the same as that in Experiment 1 described above, was used as lidocaine hydrochloride, and Solution (h) of Experiment 2 was used as adrenaline. Solution (b) of Experiment 1 was used as dexmedetomidine. The solutions were used to prepare reagents as shown in Table 13.

TABLE 13

|  | Solution 32 (Control) | Solution 33 | Solution 34 |
|---|---|---|---|
| Japanese Pharmacopoeia adrenaline injection | None | Solution (h) 1.0 ml | Solution (h) 1.0 ml |
| Lidocaine hydrochloride | Solution (e) 1.0 ml | Solution (e) 1.0 ml | Solution (e) 1.0 ml |
| Physiological saline | 3.0 ml | 2.0 ml | 1.0 ml |
| Dexmedetomidine hydrochloride | None | None | Solution (b) 1.0 ml |

Experimental Method:

Hartley male guinea pigs each having a body weight of 500 to 600 g were intraperitoneally injected with 20 mg of a pentobarbital sodium injection (Nembutal injection, Dainippon Sumitomo Pharma Co., Ltd., Osaka) as a general anesthetic drug and were set in an immobilized state. The hair of the back was clipped and then three sites around the center of the back were marked with a felt-tipped pen at sufficient intervals. A blood flow value was measured by attaching a Doppler rheometer (ALF21RD; ADVANCE CO., LTD., Tokyo) probe and was used as a baseline value (Time 0). In this case, there was found to be no difference in blood flow values of the three sites. 0.1 ml each of Solutions 32, 33, and 34 obtained by the blending was intradermally injected into the three sites and the Doppler rheometer probe was fixed on the same sites. A blood flow value was time-dependently measured at an interval of 5 minutes after the injection until 30 minutes. The ratio of the blood flow value to the baseline value (0 to 1.0) was expressed as a peripheral blood flow degree and a time-dependent change at each of the injection sites was determined.

As a result, as illustrated in FIG. 2, Solution 33 (0.5% lidocaine supplemented with adrenaline at a final concentration of $1\times10^{-6}$ M) was found to show a markedly lower blood flow as compared to Solution 32 (0.5% lidocaine: control). However, Solution 34 (mixture of 0.5% lidocaine supplemented with adrenaline at a final concentration of $1\times10^{-6}$ M and dexmedetomidine at a final concentration of $1\times10^{-7}$ M) suppressed peripheral vasoconstriction caused by adrenaline, suggesting that dexmedetomidine suppressed the peripheral vasoconstriction action of adrenaline.

The above-mentioned results showed that dexmedetomidine tended to suppress the peripheral vasoconstriction action of adrenaline. In fact, a negative feedback function against an action via an α1 adrenoreceptor is known as an action of an α2 adrenoreceptor to which dexmedetomidine specifically binds. The results suggest that a synergistic effect of a local anesthesia enhancing action by dexmedetomidine and adrenaline does not result from a vasoconstriction action enhancing effect but results from an unexpected mechanism.

INDUSTRIAL APPLICABILITY

As described above in detail, when adrenaline or a salt thereof is added to a local anesthetic agent and is used, the use of the composition for local anesthesia including an α2 receptor agonist of the present invention allows the dilution of the concentration of adrenaline or a salt thereof to be used by 5-fold or more, leading to a reduction in amount to be used. The composition for local anesthesia of the present invention exhibits a strong local anesthesia enhancing action without increasing an adverse effect as compared to using adrenaline or a salt thereof alone by devising the mixing ratio of an α2 receptor agonist (for example, dexmedetomidine) to adrenaline or a salt thereof. Applications of surgeries and treatments which can be performed under local anesthesia can be expected to be enlarged. If surgeries and treatments, which has conventionally been performed under general anesthesia, can be performed under local anesthesia, and further, day surgeries become possible, a reduction in medical care cost can be achieved as well.

The composition for local anesthesia of the present invention enhances an anesthetic action due to local anesthesia and is applicable to surgeries, treatments, and dental therapies, each of which requires a long-term local anesthetic action. Further, in addition of the foregoing, the composition for local anesthesia is also applicable to pain clinics. For example, applications to the control and palliative care of cancer pain can also be expected.

The composition for local anesthesia of the present invention can provide safe local anesthesia while retaining a sufficient local anesthetic action because an equivalent local anesthesia enhancing action is obtained even when the amount of adrenaline or a salt thereof is reduced as compared to a conventional addition amount of adrenaline or a salt thereof alone. The composition for local anesthesia of the present invention can provide safe local anesthesia to, for example, older people and patients who experience undesirable actions at a conventional use concentration. The composition for local anesthesia of the present invention has large advantages for those people and hence can contribute to medical therapies not only in the Japanese society with long living people, in which older people and patients are increasing, but also in the world.

Further, the local anesthetic agent formulation obtained by formulating the local anesthetic agent and the composition for local anesthesia in advance is convenient in that the local anesthetic agent and the composition for local anesthesia do not need to be blended in medical practice. In addition, the kit for local anesthesia including the local anesthetic agent and the composition for local anesthesia as components needs to be blended before use but is convenient in that the blending ratio may be appropriately adjusted as necessary.

The invention claimed is:

1. A composition for local anesthesia to be added to a local anesthetic agent, the composition comprising adrenaline or a salt thereof at a concentration of $1\times10^{-20}$ M to $2.7\times10^{-5}$ M, and dexmedetomidine or a salt thereof at a concentration of $1\times10^{-15}$ M to $1\times10^{-6}$ M.

2. A local anesthetic agent formulation, comprising lidocaine or a salt thereof and the composition for local anesthesia according to claim 1.

3. A kit for local anesthesia, comprising lidocaine or a salt thereof and the composition for local anesthesia according to claim 1 as components.

* * * * *